US005730276A

United States Patent [19]
Itoh

[11] Patent Number: 5,730,276
[45] Date of Patent: Mar. 24, 1998

[54] TEST OBJECT CONTAINER HOLDER AND HOLDER CONVEYER APPARATUS

[76] Inventor: Teruaki Itoh, 5-25, Kokaihommachi, Kumamoto-shi, Kumamoto-ken, Japan

[21] Appl. No.: 603,067

[22] Filed: Feb. 20, 1996

[30] Foreign Application Priority Data

Feb. 20, 1995 [JP] Japan .................... 7-030888

[51] Int. Cl.$^6$ ................................ B65G 29/00
[52] U.S. Cl. .................................... 198/465.1
[58] Field of Search ...................... 198/465.1, 358, 198/803.01, 803.11, 803.15, 459.6

[56] References Cited

U.S. PATENT DOCUMENTS

| | | | |
|---|---|---|---|
| 4,958,667 | 9/1990 | Rece et al. | 198/803.15 X |
| 5,127,509 | 7/1992 | Kohlen et al. | 198/465.1 X |
| 5,289,910 | 3/1994 | Kohlen et al. | 198/465.1 X |
| 5,335,776 | 8/1994 | Backhaus | 198/465.1 X |
| 5,346,058 | 9/1994 | Santandrea et al. | 198/803.01 |

Primary Examiner—James R. Bidwell
Attorney, Agent, or Firm—Nixon & Vanderhye

[57] ABSTRACT

The test object container holder of the present invention comprises a holder body having a container storage portion, a first ring groove, and a second ring groove, and an indication ring engaged in the outer circumference of the holder body. The test object container holder conveyer apparatus of the present invention includes a test object container holder including a holder body and an indication ring, holder conveyer, for conveying the test object container holder, a sensor for detecting and notifying the indication ring, a convey pause mechanism operated in response to an output from the sensor, an orientation control mechanism for orienting the paused test object container holder in a predetermined direction, a read device for reading information of the indication ring, and command device for supplying the test object container holder with a necessary command.

9 Claims, 6 Drawing Sheets

FIG. 12

TEST OBJECT CONTAINER HOLDER AND HOLDER CONVEYER APPARATUS

BACKGROUND OF THE INVENTION

1. Field of the Invention

The present invention relates to a test object container holder for stably holding a test object container such as a test tube or the like which contains a test object such as blood, and also relates to a holder conveyer apparatus for conveying the test object container holder to a predetermined position to perform a predetermined treatment.

2. Description of the Related Art

As a test object container holder of this kind, the present inventor has already proposed a holder which has a container receive hole capable of holding a test object container, in the axial portion of a cylindrical body, which has a first ring groove to be engaged with a guide edge of a convey path, in the vicinity of a top portion of the the outer circumferential surface of the cylindrical body, and which has a second groove in the vicinity of the outer circumferential surface of the cylindrical body, for allowing insertion of an operation rod in a convey pause mechanism provided in the convey path. Further, as an apparatus for conveying this test object container holder, the present inventor has already proposed a holder conveyer apparatus which comprises a belt conveyer mechanism capable of conveying the test object container holder containing a test object container, and a guide mechanism having a guide edge which is engaged, on both sides, with the first ring groove of the test object container holder conveyed by the belt conveyer mechanism.

A conventional test object container holder as described above has the following problems. Namely, test object containers are provided with identification bar-code labels stuck thereon which record types, treatment methods and the likes of the test bodies contained in the containers. However, the conventional test object container holder itself does not have any specific indications.

Therefore, to detect arrival of a test object container holder at a predetermined position, the test object container holder itself must be detected by any measures. However, in case where the test object container holder is made of material such as synthetic resin, it is difficult to detect the holder, so that the detection sensitivity is low and detection errors are caused, for instance, even when detection is achieved with use of a photo-sensor or the like. To prevent those detection errors, a high sensitivity sensor of high costs is required.

In addition, where several test tubes of different diameters are used as test object containers, test object container holders suitable for the diameters must be prepared. Preparation of different kinds of test object container holders, however, is wasteful in view of their manufacture and management, and suggests many economical problems. In addition, operation for proper use of these holders itself is complicated, and may cause difficulties in conveying the test object containers.

Meanwhile, a conventional test object container holder conveyer apparatus has the following problems. That is, to pause conveying of a test object container holder, the conveyer mechanism must always be stopped temporarily. This results in a drawback that other test object holders are stopped when only a desired test object container holder is to be paused. Besides, the conveyer mechanism thus often repeats start and stop operations, and the start and stop operations seriously cause noise and damage respective components.

Also, in a conventional test object container holder conveyer apparatus, the test object containers are driven to rotate with use of a rotation drive source in order to orient information record areas such as bar-code levels in the reading direction. Therefore, the structure of the apparatus is complicated, is lack of reliability, and requires high costs.

SUMMARY OF THE INVENTION

The object of the present invention is to provide a test object container holder and a holder conveyer apparatus as follows.

(a) A test object container holder which is capable of precisely detecting arriving at or passing-through a predetermined position by means of a simplified sensor of a relatively low price.

(b) A test object container holder of a common type which is capable of stably holding test object containers even if test tubes having different diameters are used as test object containers.

(c) A holder conveyer apparatus comprising a convey pause mechanism which is capable of surely pausing only a test object container holder at a specified position without pausing the conveyer mechanism.

(d) A holder conveyer apparatus comprising an orientation control mechanism having a simple structure, which is capable of rotating a test object container holder pausing at a specified position without using any specific rotation drive source and is capable of orienting an information recording area stuck on a test object container in a desired direction.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

To achieve the above object, the test object container holder and the holder conveyer apparatus according to the present invention is constructed in the following structure.

(Test Object Container Holder)

The test object container holder according to the present invention comprises a holder body and an indication ring, the holder body including a container storage portion capable of holding a test object container in an axial portion of a cylindrical base, a first ring groove near the top of the outer circumferential surface of the cylindrical base, to be engaged with guide edges of a convey path, and a second ring groove near the bottom of the outer circumferential surface of the cylindrical base, which allows insertion of an operation rod in a convey pause mechanism, and the indication ring being engaged in the outer circumference of the holder body and indicating presence of the holder body.

The holder body is preferably made of resin material and the indication ring is made of metal. In addition, a container storage portion preferably comprises a container storage hole provided so as to store a lower region of the test object container including at least the bottom thereof, and a connection hole provided so as to connect the bottom inner surface of the container storage hole with the outer surface of the holder body. In addition, the test object container holder preferably comprises an adapter member for a container of a different diameter which is installed on the open end of the container storage portion. The adapter member comprises a brim-like elastic member which has a projecting portion in its inner peripheral portion and projects in the direction toward the center thereof.

According to the test object container holder of the present invention, a test object container holder is conveyed with the first ring groove being engaged with the guide edges of the convey path. Therefore, even when the test object container holder having a cylindrical shape standing vertically undergoes a vibration or the like while conveying the holder, undesired accidents can be prevented, e.g., the test object container holder is prevented from turning over. In addition, since an operation rod is inserted at a specified position on the convey path into an area of the second ring groove in the forward side of a predetermined test object container holder being conveyed in the conveying direction, the predetermined test object container holder can be easily and accurately stopped. Further, to detect the test object container holder, it is only necessary to simply detect an indication ring having a ring shape, and as a result, more accurate detection is achieved in comparison with a case where the test object container holder itself is detected. In addition, since the indication ring has a circular ring shape, detection of the test object container holder (e.g., arrival of a test object container holder at a specified position and counting of the number of holders) can always be performed stably regardless of the direction in which the test object container holder is oriented. Note that a metal sensor of low costs can be adopted when the indication ring is made of metal. If the holder body is made of resin material, the holder body has a slight elasticity and is suitable for holding a test object container made of glass. Further, if the container storage portion comprises a container storage hole and a connection hole, air inside the storage hole freely enters and comes out through the connection hole when the test object container such as a test tube or the like is inserted or pulled out. As a result, air inside the container storage hole is not compressed or the inside of this hole is not evacuated, and therefore, insertion and pulling of the test object container can be smoothly performed. In case where an adapter member for a container of different diameter is attached to the open end of the container storage portion, a test object container can be stored and held with use of a test object container holder of one same type due to function of the adapter member even when a test tube having a diameter different from the other ordinary test object containers is used as a test object container.

(Apparatus for Conveying a Test Object Container Holder)

The apparatus for conveying a test object container holder, according to the present invention comprises: a test object container holder including a holder body and an indication ring, the holder body having a container storage portion at an axial portion of a cylindrical base such that the container storage portion is capable of holding the test object container, a first ring groove near the top of the outer circumferential surface of the cylindrical base, to be engaged with guide edges of the convey path, and a second ring groove near the bottom of the outer circumferential surface of the cylindrical base, which allows insertion of the operation rod in the convey pause mechanism, and the indication ring being engaged in the outer circumference of the holder body and used to indicate presence of the holder body; a holder conveyer means including a conveyer mechanism provides so as to be capable of conveying the test object container holder, and a guide mechanism provided on both sides of the conveyer mechanism such that guide edge portions of the upper end of the side wall portions are engaged with the first ring groove of the test object container holder; a holder detection sensors which detect the indication ring of the test object container holder conveyed to a specified position by the holder conveyer means and output information indicating arrival of the test object container holder at the specified position; a convey pause mechanisms are operated on the basis of the output from these sensors, thereby to insert an operation rod into an area positioning in the forward side of the holder in the forward direction in the second groove of the test object container holder; an orientation control mechanism for controlling the test object container holder paused by the convey pause mechanism such that an information record area of the test object container stored and held by the holder is oriented in a predetermined direction, by rotating the holder around the holder axis as the center of rotation; a read device 40 provided so as to read record information of the information record area whose orientation is controlled by the orientation control mechanism; and a command means supplies the test object container holder with a necessary command on the basis of the information read by the read device.

The conveyer apparatus of the present invention preferably comprises a means for making the convey pause mechanism operate with the belt of a belt-type conveyer mechanism being moved, thereby to pause convey operation at a specified position with the test object container holder slipping at the specified position on the belt. In addition, the apparatus preferably comprises a means for pressing downwardly the top eccentric position of the test object container holder paused at a specified position, slipping on the belt, thereby to incline the test object container holder to apply a rotation torque based on the belt movement.

In the conveyer apparatus described above, when the test object container holder storing the test object container is conveyed to a specified position by the conveyer mechanism, the indication ring of the test object container holder is accurately detected by the sensors, which output a signal indicating arrival of the test object container holder. Then, the convey pause mechanism is operated so as to insert the operation rod into an area of the second ring groove positioned in the forward side of the holder in the forward direction of the holder, so that the test object container holder is paused at the specified position. The test object container holder thus paused is driven to rotate around the holder axis as the center of rotation by the orientation control mechanism, and is controlled such that the information record area (e.g., the area where a bar-code label is stuck) is oriented in a predetermined direction (i.e., the sensor arrangement direction). Further, in the above test object container holder convey apparatus, only a predetermined test object container holder can be paused at a specified position with the conveyer mechanism being operated, so that other test object container holders than the predetermined test object container holder can be continuously conveyed. In addition, since the conveyer mechanism does not frequently repeat start and stop operations, it is possible to reduce generation of noise and damages of respective components accompanied by start and stop operations of the conveyer mechanism. Further in the test object container holder conveyer apparatus, when the top eccentric position of the test object container holder is pressed downwardly, thereby inclining the test object container holder, a deviated portion of the bottom of the test object container holder is more strongly pressed against the belt of the conveyer mechanism than against the other portions. Thus, a rotation torque based on the moving force of the belt is generated at the test object container holder paused at a specified position, so that the test object container holder is driven to rotate. Hence, it is not necessary to provide any special driving source and the structure of the apparatus is simplified accordingly.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 3 and 4 are views showing the structure of a test object container holder according to the first embodiment of the present invention, wherein

FIGS. 5 to 7 are views showing the structure of the test object holder according to a second embodiment of the present invention, wherein

FIGS. 8 and 9 are views for explaining basic operation of the test object container holder according to the first and second embodiment, wherein

DETAILED DESCRIPTION OF THE PREFERRED EMBODIMENTS (First Embodiment)

Figure 1:
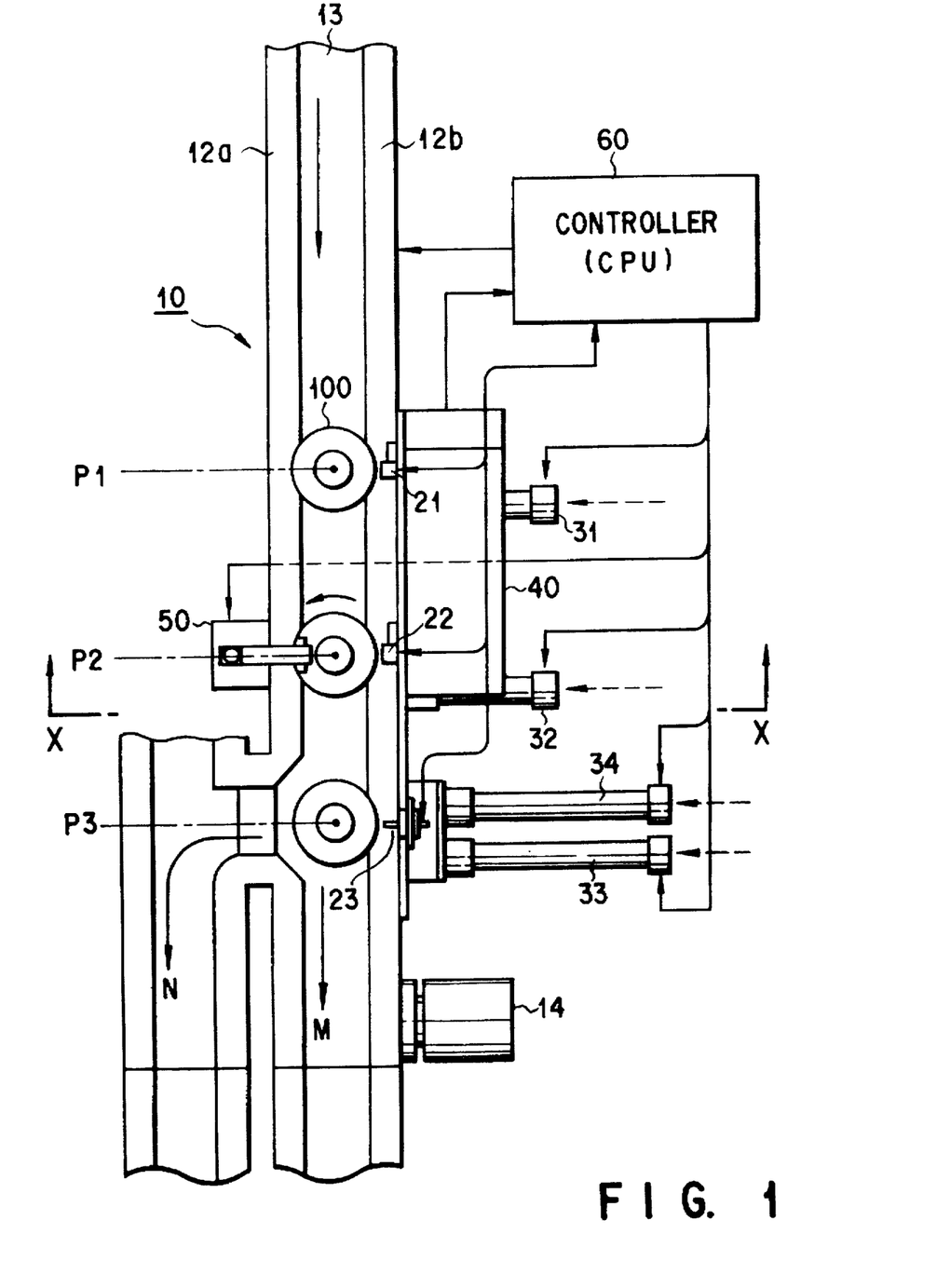
FIG. 1 is a plan view showing the structure of a test object container holder conveyer apparatus according to a first embodiment of the present invention.
Figure 2:
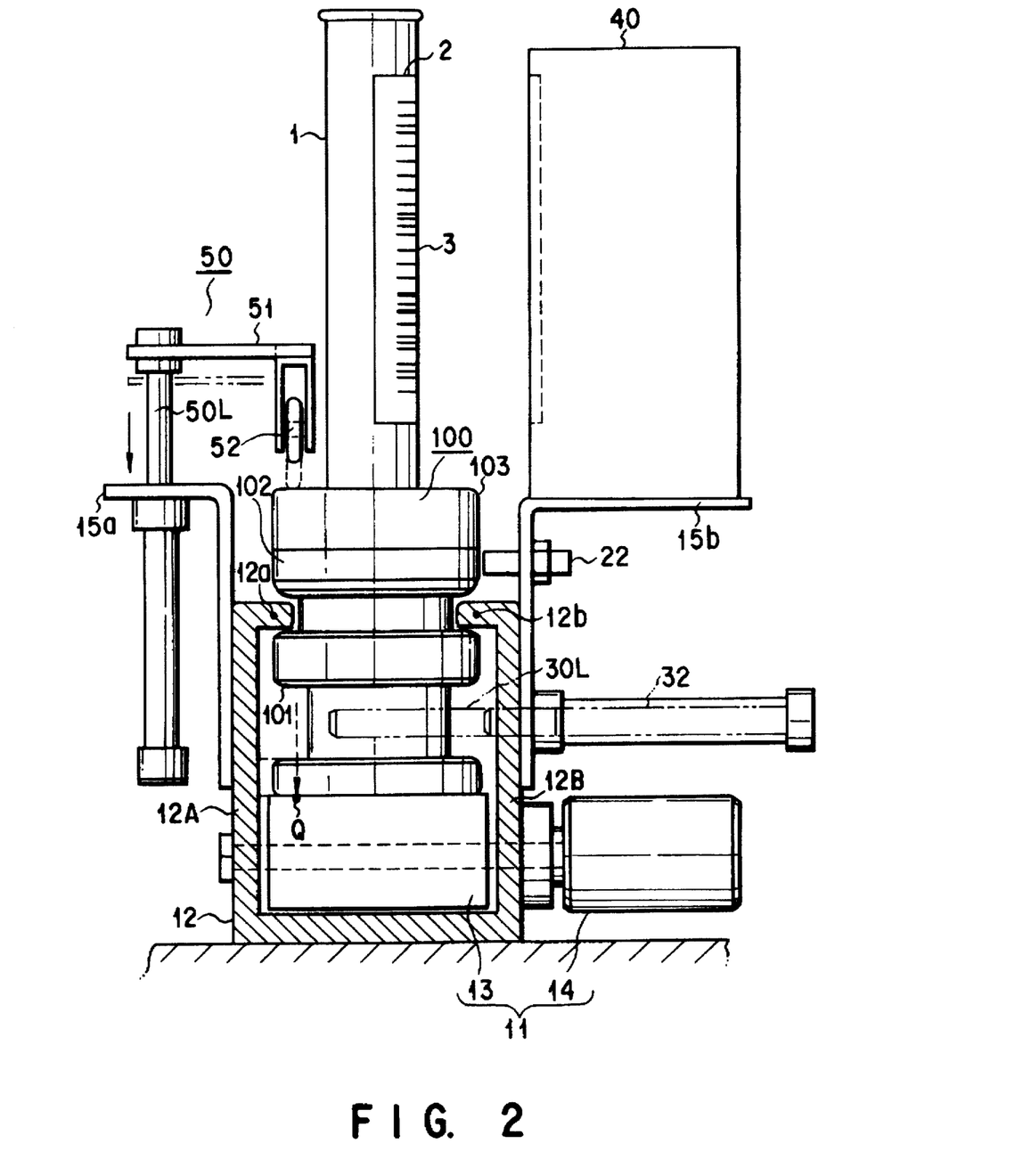
FIG. 2 is a cross sectional view cut along X—X line of FIG. 1 viewed from the arrow direction, showing the structure of a test object container holder conveyer apparatus according to the first embodiment of the present invention.

FIG. 1 is a plan view schematically showing a test object container holder conveyer apparatus according to the first embodiment of the present invention, and FIG. 2 is a front view showing a main part of the same.

In FIGS. 1 and 2, the reference 10 is a holder conveyer means comprising a belt type conveyer mechanism 11 and a guide mechanism 12. The conveyer mechanism 11 is, for example, arranged such that an endless belt 13 made of urethane or the like is driven and rotated by a motor 14 and such that a test object container holder 100 described later can be conveyed. In addition, the guide mechanism 12 is constructed such that guide edge portions 12a and 12b which are engaged with a first ring groove 121 of the test object container holder 100 described later are respectively provided inside top ends of side walls 12A and 12B standing on both sides of the above-mentioned conveyer mechanism 11. Note that the guide mechanism 12 and endless belt 13 constitute a conveyer path (lane) of the present invention.

Holding plates 15a and 15b of inverted L-shape are respectively provided on the outer surfaces of both side walls 12A and 12B of the guide mechanism 12. For example, holder detection sensors 21 and 22 having magnet type metal sensors and a holder detection sensor 23 having a reflection type photo-sensor are provided with predetermined distances inserted therebetween, on the vertical portion of the holding plate 15b positioned in the right-hand side in FIGS. 1 and 2. Each of these holder detection sensors 21, 22, and 23 detects an indication ring 102 made of steel of a test object container holder 100 described later which has been conveyed to a specified position by the holder conveyer means 10 described above, and outputs detection information thereof to a control device 60.

Conveyance pause mechanisms 31, 32, and 33 and a convey direction change mechanism 34 are installed on the vertical portion of the holding plate 15b. Each of the convey pause mechanisms 31, 32, and 33 and the convey direction change mechanism 34 comprises an air piston/cylinder device as a main part.

The convey pause mechanisms 31, 32, and 33 are respectively driven and controlled on the basis of control signals supplied from a controller 60, which is a central processing unit (CPU), which operates on the basis of outputs from the holder detection sensors 21, 22, and 23. The convey pause mechanisms 31, 32, and 33 cause an operation rod 30L connected to a piston portion to project while being driven, and insert this rod into an area positioned in the forward direction side of the holder described above in a second ring groove 122 of the test object container holder 100 described later, thereby pausing the holder 100.

In this embodiment, conveyer pause mechanisms 31, 32, and 33 are operated with a belt type conveyer mechanism 11 being moved, thereby to make the test object container holder 100 slip at a specified position so that conveying operation is stopped temporarily.

The convey direction change mechanism 34 comprises an operation rod (not shown) whose top has a shape suitable for moving the test object container holder 100 in a direction perpendicular to the running direction. When the convey direction change mechanism 34 is driven and controlled on the basis of a control signal from the controller 60, the mechanism 34 makes the operation rod project so as to press the second ring groove 122 the test object container holder 100, thereby to move the test object container holder 100 in the direction perpendicular to the running direction.

A bar-code reading device 40 is mounted and fixed on the horizontal portion of the holding plate 15b. This bar-code reading device 40 reads record information (i.e., a bar-code) in the information record area (i.e., the stuck position of the bar-code label) 2 of the test object container 1 whose orientation is controlled, and sends the information thus read to the controller 60. By a control signal from the controller 60 which operates on the basis of information read out by the reading device 40, the convey direction change mechanism 34 is operated and supplies a necessary command (e.g., a command for moving the holder 100 in the direction perpendicular to the running direction) to the detection container holder 100.

On the other hand, an orientation control mechanism 50 is installed on the holding plate 15a illustrated in the left-hand side in FIGS. 1 and 2. This orientation control mechanism 50 rotates the test object container holder 100 which is paused by the convey pause mechanism 32, around the holder axis, thereby to control the information record area 2 (i.e., the position where the bar-code label is stuck) so as to be oriented in the predetermined direction (i.e., the direction of the bar-code reading device 40). The orientation control mechanism 50 also comprises an air piston/cylinder device as its main part. The orientation control mechanism 50 draws the operation rod 50L connected to the piston section while being operated, in the arrow direction, and presses the press roller 52 installed on the top of the operation rod 50L through a spring member 51, against the top eccentric position of the test object container holder 100, thereby to make the test object container holder 100 generate a rotation torque based on the movement of the belt.

Specifically, the orientation control mechanism 50 described above presses downwardly the top eccentric position of the test object container holder 100 whose conveying is paused by the convey pause mechanism 32, while making the holder slipping at a specified position on the belt 13, so that the test object container holder 100 is slightly inclined thereby generating a friction force concentrated on the eccentric position of the holder bottom in accordance with the movement of the belt 13, thereby to apply a rotation torque to the test object container holder 100.

Figure 3:
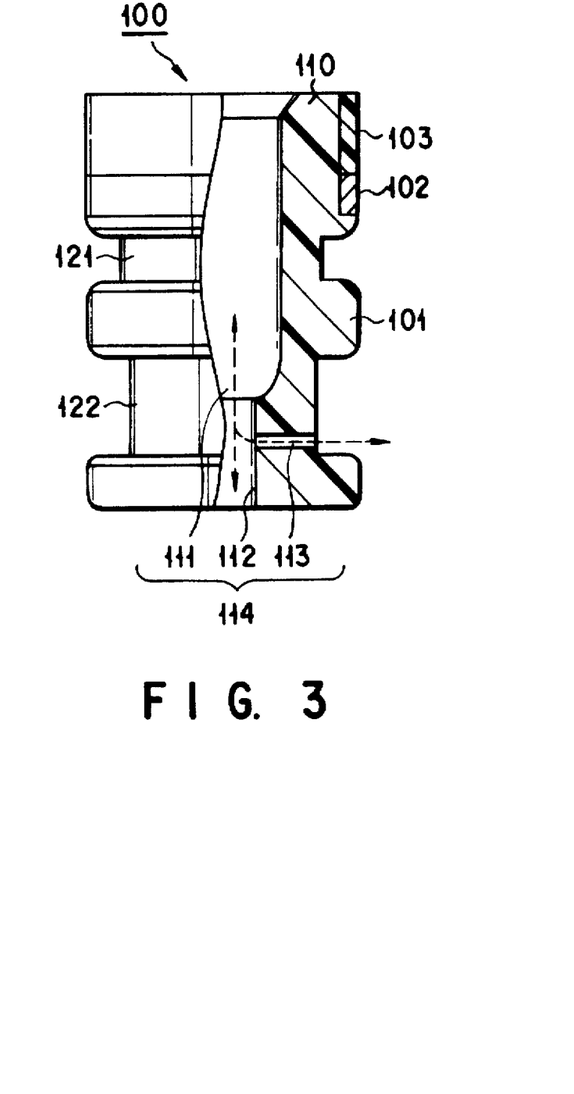
FIG. 3 is a side view showing the right half section thereof cut out and FIG. 4 is a side view showing the right half section thereof cut out with respective components developed.
Figure 4:
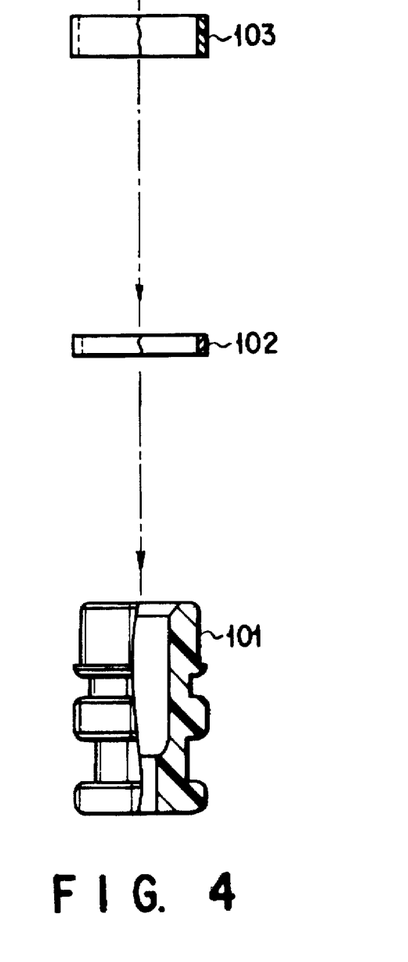

FIGS. 3 and 4 are views showing the structure of the test object container holder according to the first embodiment of the present invention, wherein FIG. 3 is a side view showing the right half cut out and FIG. 4 is a side view showing respective parts developed.

As shown in FIGS. 3 and 4, the test object container holder 100 comprise a holder body 101, an indication ring 102 which is engaged with the outer circumference of the holder body 101 and a fixed cap 103. The indication ring 102 is made of metal material (e.g. Ferrous in this case) for indicating presence of the holder body 101.

The holder body 101 has a container storage portion 114 at the axial portion of a cylindrical base 110 integrally formed of resin material such as polyacetal. The holder body 101 also has a first ring groove 121 near the top portion of the outer circumferential surface of the cylindrical body 110, and the groove 121 is engaged with guide edges 12a and 12b. Further, the holder body 101 has a second ring groove 122 near the bottom of the outer circumferential surface of the cylindrical base, and the groove 122 allows insertion of the operation rod 30L in the convey pause mechanisms 31, 32, and 33 provided in the guide mechanism 12.

The container storage portion 114 comprises a container storage hole 111 arranged so as to contain at least the lower region including the bottom of the test object container 1 such that the read device 40 reads record information (or bar-code) 3 on information record area (at the sticking position of the bar-code label) of the test object container, a main connection hole 112 arranged so as to connect the bottom inner surface of the container storage hole 111 and the outer surface of the holder body 101, and a sub connection hole 113 arranged so as to extend in the direction orthogonal to the main connection hole 112.

A fixed cap 103 is, for example, made of the same material as that of the holder body 101, and is engaged with the outer circumference of the holder body 101 with appropriate coating material applied thereon. Note that the fixed cap 103 may be of a screw type.

Explanation will be made to operation of the test object container holder conveyer apparatus. At first, the holder conveyer means 10 is operated, and then, the test object container holder 100 which contains and holds the test object container 1 in the container storage hole 111 is moved to a position P1 of FIG. 1 by the belt conveyer mechanism 13. When the test object container holder 100 arrives at the position P1, the holder detection sensor 21 detects an indication ring 102 of the test object container holder 100 described above, and sends detection information to the controller 60. Accordingly, the controller 60 supplies an operation control signal to the convey pause mechanism 31. The convey pause mechanism 31 is thereby operated so as to make the operation rod 30L project, so that the test object container holder 100 is paused at the position P1, while being slipped on the moving belt 13. In this state, the holder detection sensor 22 confirms whether or not another test object container holder 100 is present at a position P2. When the absence of another test object container holder 100 at the position P2 is confirmed, operation of the convey pause mechanism 31 recovers. Therefore, the test object container holder 100 paused at the position P1 starts moving again. When presence of another test object container holder 100 at the position P2 is confirmed, the test object container holder 100 waits at the position P1 until another test object container holder 100 leaves the position P2.

When the test object container holder 100 which thus restarted moving arrives at the position P2, the holder detection sensor 22 detects the indication ring 102 of the test object container holder 100 and sends detection information to the controller 60. Then, the controller 60 supplies an operation control signal to the convey pause mechanism 32. Therefore, the convey pause mechanism 32 starts operating and makes the operation rod 30L project. As a result, the test object container holder 100 is paused at the position P2, while slipping on the belt 13 moving. In this state, an operation control command is supplied to the orientation control mechanism 50 from the controller 60, the orientation control mechanism 50 starts operating. Then, the press roller 52 of the orientation control mechanism 50 presses the top eccentric position of the test object container holder 100. Hence, the press roller 52 installed on the top of the operation rod 50L via the spring member 51, the press roller 52 is pressed in stable contact with the top eccentric position of the test object container holder 100 at a predetermined elasticity.

Thus, the test object container holder 100 is slightly inclined in the left-hand side in FIG. 2, and weights are concentrated on the eccentric point Q on the bottom surface. As a result of this, a rotation torque is caused in accordance with the movement of the belt 13. Therefore, the test object container holder 100 rotates together with the test object container 1 around the holder axis as the center of rotation. In accordance with the rotation, the information record area (where the bar-code label is stuck) 2 on the circumference of the test object container 1 passes in the direction of the bar-code reading device 40 at a predetermined speed, facing the device 40. As a result, relative read scanning is performed and the information thereon is read out by the bar-code read device 40. Upon completion of this reading operation, a control signal from the control device 60 is cut, and the convey pause mechanism 32 recovers and operates. Therefore, the test object container holder 100 restarts moving. When the test object container holder 100 arrives at the position P3, the holder detection sensor 23 consisting of a reflection type photo-sensor detects the indication ring 102 of the test object container holder 100, and supplies the detection information to the controller 60. Then, the controller 60 supplies an operation control signal to the convey pause mechanism 33. Therefore, the convey pause mechanism 33 is operated to make the operation rod 30L project. As a result, the test object container holder 100 is paused at the position P3 while slipping on the belt 13 moving.

In this state, the controller 60 supplies a control signal corresponding to information read by the reading device 40. As a result of this, for example, operating state of the convey pause mechanism 33 is released or the convey direction change mechanism is driven. When the operating state of the convey pause mechanism 33 is released, the test object container holder 100 moves linearly in the direction of arrow M of FIG. 1. In addition, when the convey direction change mechanism 34 is driven, the test object container holder 100 is pushed in the direction perpendicular to the convey direction, and is thus shifted to a convey path (or a lane) adjacent thereto. Therefore, the test object holder 100 is finally conveyed as indicated by the arrow N of FIG. 1.

(Second Embodiment)

Figure 5:
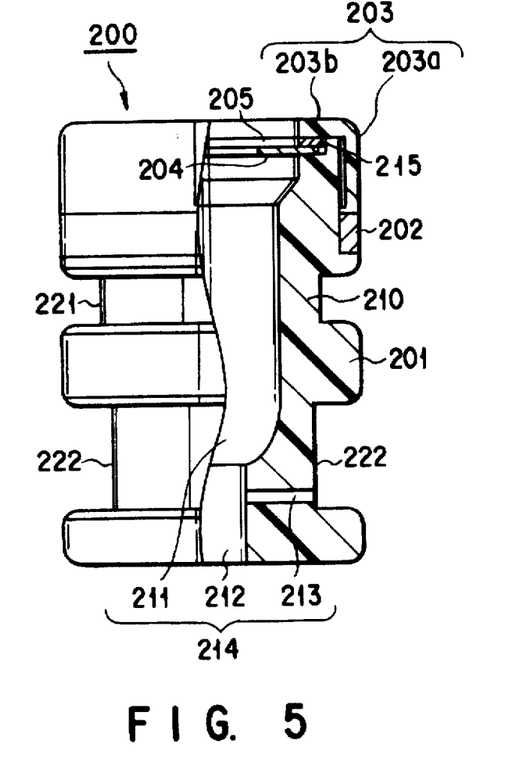
FIG. 5 is a side view showing the right half section thereof cut out.
Figure 6:
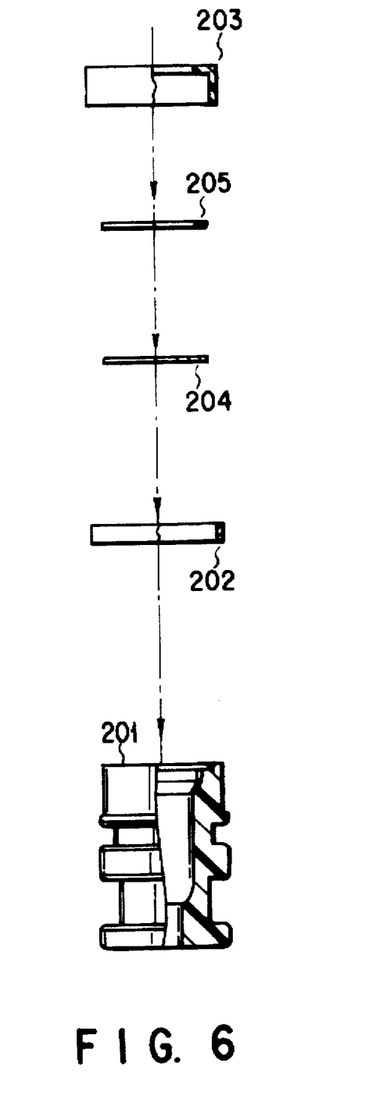
FIG. 6 is a side view showing the right half section cut out with respective components developed and FIG. 7 is a plan view showing an adapter member for a container of a different diameter.
Figure 7:
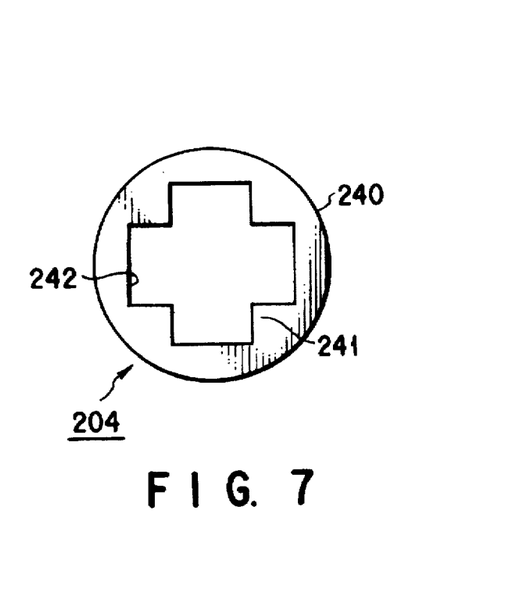

FIGS. 5 to 7 are views showing the structure of the test object container holder according to the second embodiment of the present invention. FIG. 5 is a side view showing the right half cut. FIG. 6 is a side view showing the right half cut out with respective components developed. FIG. 7 is a plan view of an adapter member for a container of a different diameter.

As is shown in FIGS. 5 to 7, the test object container holder 200 comprises a holder body 201, an indication ring 202 made of metal and engaged in the outer circumference of the holder body 201, for indicating presence of the holder body 201, a screw type fixing cap 203, an adapter member 204 for a container of different diameter, and a rotation stopper member 205.

The holder body 201 has a container storage portion 214 capable of storing the test object container 1, at the axis portion of the cylindrical base 210 made of resin material such as polyacetal, like in the first embodiment. The holder body 201 has a first ring groove 221 near the top of the outer circumferential surface of the cylindrical base 210, and a second ring groove 222 near the bottom of the outer circumferential surface of the cylindrical base 210. The first ring groove is engaged with the guide edges 12a and 12b of the guide mechanism 12, and the second ring groove 222 allows insertion of the operation rod 30L in the convey pause mechanisms 31, 32, 33 provided at the guide mechanism 12. Note that a gap portion 215 is formed at the upper open end of the container storage portion 214.

The container storage portion 214 comprises a container storage hole 211 provided to be capable of holding a lower region of the test object container 1 at least including the bottom of the test object container 1, a main connection hole for connecting the inner side of the bottom of the container storage hole 211 with the outer surface of the holder body 201, and a sub connection hole 213 provided in the direction perpendicular to the main connection hole 212.

The adapter member 204 for a container of different diameter is formed integrally of elastic material such as natural rubber, in a shape having a plurality of (e.g., four in this case) projecting sections 241 on the inner peripheral portion of the brim-like member 240. The projecting section 241 orient to center of the brim-like member 240, as shown in FIG. 7. In other words, this embodiment uses a spits-guide having a slit-like opening portion 242 of a cross-shape. This adapter member 204 for a container of a different diameter is detachably installed on the gap portion 215 formed at the upper open end of the container storage portion 214 in the holder body 201.

The fixed cap 203 comprises a cylindrical portion 203a which can be screwed on the top of the holder body 201, and a fringe portion 203b projecting into the upper end opening portion of the cylindrical portion 203a. The cap 203 presses the indication ring 202 engaged in the outer circumference of the holder body 201 at the base end portion of the cylindrical portion 203a, and presses the peripheral portion of the adapter member 204 for a container of different diameter at the fringe portion 203b, by means of a rotation stopper member 205.

By using the test object container holder 200 of the second embodiment described above, even when different kinds of test tubes are used in mixture as test object containers 1, those test tubes of different diameters can be relatively stably contained and held due to the elastic deformation effect of the opening portion of the adapter member 204 made of elastic material, as long as the outer diameters of the test tubes are equal to or smaller than the inner diameter of the container storage hole 211 and the outer circumferential surfaces of the test tubes are of such a diameter which is pressed in contact with the top end of a convex portion 241.

FIGS. 8 to 12 are views for explaining basic operation and function of the test object container holders 100 and 200 described in the first and second embodiments. Note that, the reference numerals cited in the first embodiment are used in FIGS. 8 to 12, for conveniences.

Figure 8:
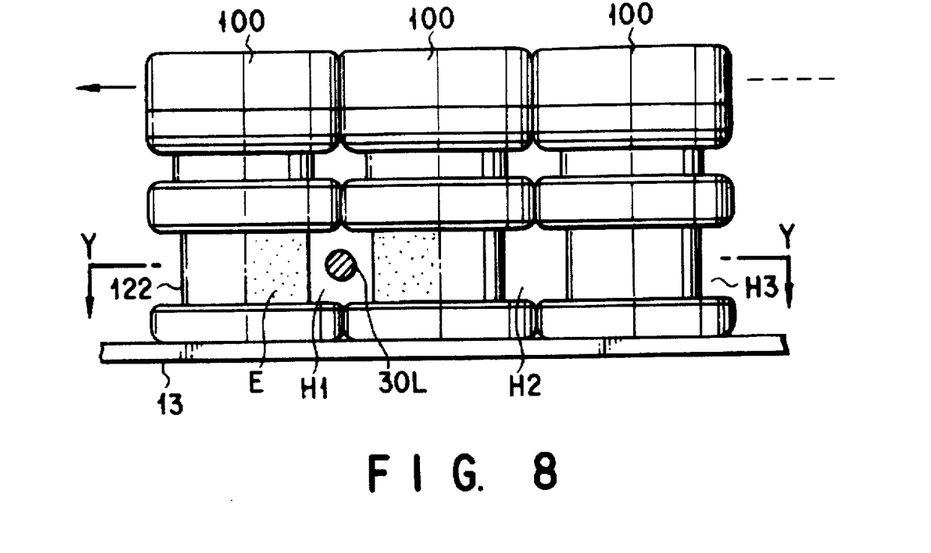
FIG. 8 is a side view showing a group of test object container holders and FIG. 9 is a cross section cut along line Y—Y of FIG. 8 viewed from the arrow direction.
Figure 9:
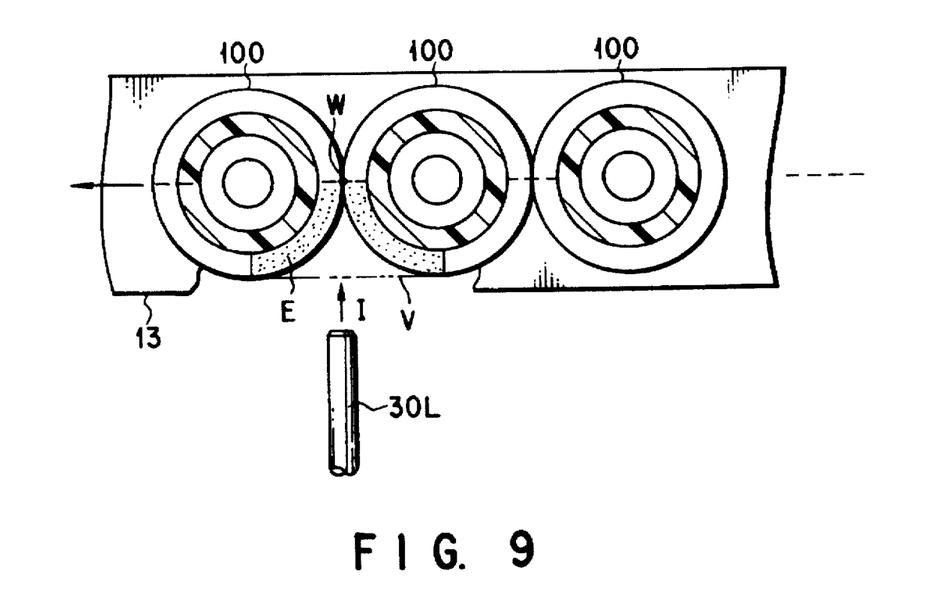

As is shown in FIG. 8, the second ring groove 122 in which the operation rod 30L is engaged has a size which allows easy insertion of the operation rod 30L. Therefore, even when a number of test object container holders 100 are conveyed in the arrow direction with themselves disposed continuously in contact and in series with each other, i.e., in a contains contact array as shown in FIG. 8, opening portions H1, H2, . . . which allow easy insertion of the operation rod 30L at adjoining area between each other of the second ring grooves 122 are provided between each other of the test object container holders 100. In addition, with respect to the above opening portions H1, H2, . . . , the shape from an end surface V where the operation rod 30L is inserted as shown in FIG. 9 to a contacting portion W to an adjacent test object container holder 100 forms an area E which is tapered like a bell mouth. Accordingly, when the operation rod 30L is inserted into an arbitrary one of opening portions H1, H2, . . . , the operation rod 30L is guided by the area E of shape like a bell mouth, so that the rod 30L can extremely smoothly slide in the opening portion. That is, each of the opening portions H1, H2, . . . comprises a guide portion for guiding insertion of the operation rod 30L.

Figure 10:
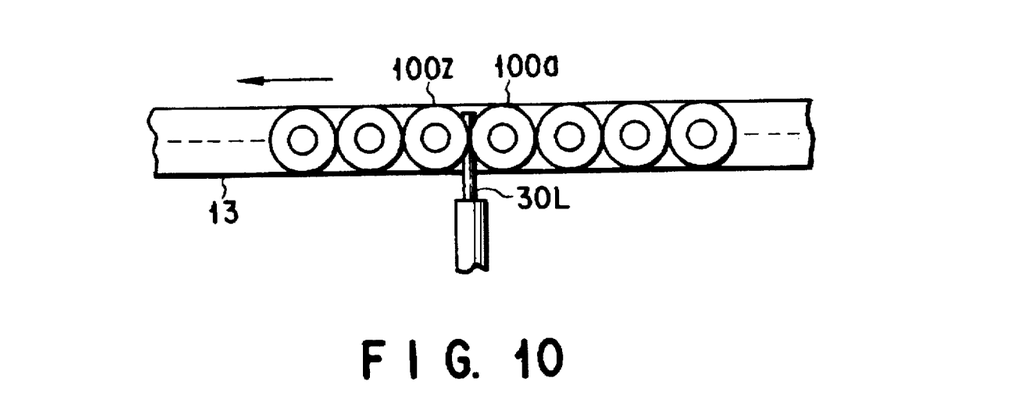
FIGS. 10 to 12 are views for explaining basic operation of the test object container holders according to the first and second embodiment of the present invention.
Figure 11:
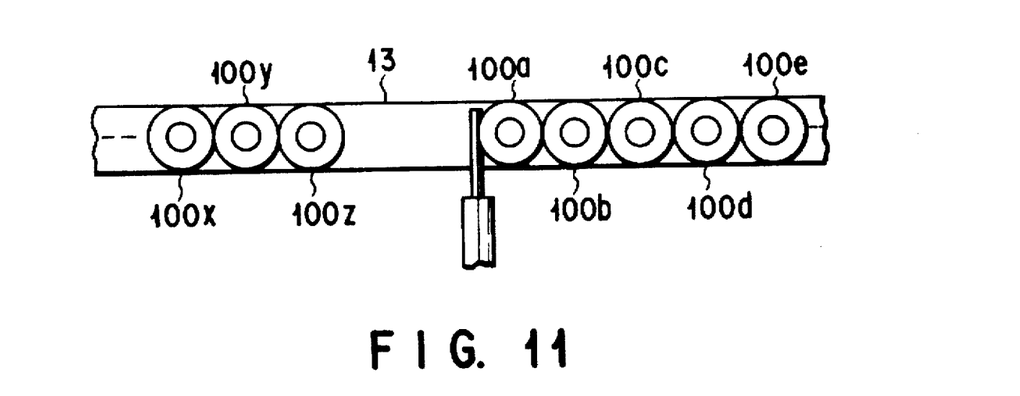
Figure 12:
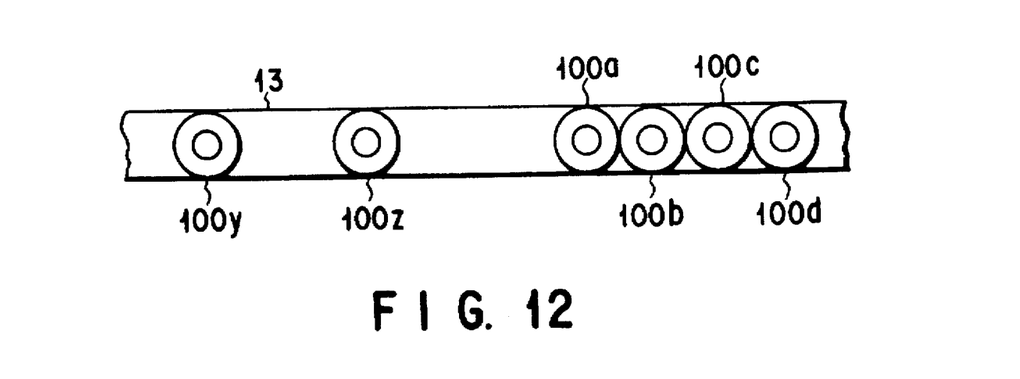

Therefore, as shown in FIG. 10, it is possible to smoothly insert the operation rod 30L into an opening portion between those two test object container holders which are positioning in the middle of the array of a number of test object container holders being conveyed in the arrow direction, e.g., the opening portion between test object container holders 100z and 100a, without disturbing the continuous contact state of the line of the test object container holders. As a result of this, as shown in FIG. 11, test object container holders positioning in an arbitrary position of the line of the test object container holders, e.g., a group of test object container holders 100z, 100y, 100x, . . . positioning in the forward side of the test object container holder 100a in the convey direction are made continuously kept in contact under convey operation, while another group of test object container holders 100a, 100b, 100c, . . . positioning in the backward side of the test object container holders in the convey direction, including the holder 100a, are made paused at a predetermined position. Since a line of a number of test object container holders continuously kept in contact with each other can thus be separated into forward and backward sides at an arbitrary position, the test object container holders 100 can be separated from each other at a predetermined interval inserted therebetween or can be separated into blocks each including a plurality of test object container holders at a predetermined interval inserted between each block. Accordingly, the holders can be conveyed in various combinations, if necessary.

(Modifications)

The test object container holder and holder conveyer apparatus according to the above embodiments include the following modifications.

\* A test object container holder which enables application of only an indication ring, or application of both an indication ring and an adapter for containers of different diameters.

\* A test object container holder whose holder body is made of material other than resin material.

\* A test object container holder which comprises an adapter for containers of different diameters which has a convex portion shaped like saw teeth in a direction toward the center of a disc plate.

\* A test object container holder which uses an indication ring made of non-ferrous material such as aluminum or brass.

\* A holder conveyer apparatus using, as a metal sensor, a high frequency oscillation type sensor capable of detecting an indication ring made of non-ferrous material.

(Summary of the Embodiments)

The structure, function, and operation of the test object container holder and holder conveyer apparatus of the present invention explained in the embodiments are summarized as follows.

[1] The holder 100 explained in the embodiment comprises a holder body 101 and an indication ring 102 which is engaged in the outer circumference of the holder body 101 and indicates presence of the holder body 101. The holder body 101 includes a container storage portion 114 capable of holding a test object container 1 in the axial portion of a cylindrical base 110, a first ring groove 121 near the top of the outer circumferential surface of the cylindrical base 110, to be engaged with guide edges 12a and 12b of the convey path, and a second ring groove 122 near the bottom of the outer circumferential surface of the cylindrical base 110, which allows insertion of an operation rod 30L in convey pause mechanisms 31, 32, 33 . . . .

Therefore, in the test object container holder 100 described above, since the holder is conveyed with the first ring groove 121 engaged with guide edges 12a and 12b of the convey path, it is possible to prevent an accident from occurring, e.g., prevent a cylindrical test object container holder 100 from turning over due to vibration caused during conveying. As a result of this, every single test object container 1 such as a test tube inserted in a container storage portion 114 can be stably conveyed to a predetermined position.

In addition, when an operation rod 30L is inserted into an area of the second ring groove 122 positioned in the forward side in the convey direction at a specified position on the convey path, a desired test object container holder 100 is paused at the specified position. In this state, the operation rod 30L is inserted into the second ring groove 122 which is positioned lower than the first ring groove 121 engaged with the guide edges 12a and 12b. Therefore, accidents can be prevented during pausing operation, e.g., a holder is prevented from turning over by shock due to pausing operation. In addition, even if the test object container holders 100 are conveyed continuously kept in contact with each other, opening portions each having a size greater than the diameter of the operation rod 30L are prepared by the second ring groove 122 between the test object container holders, so that the operation rod 30L can be inserted without problems. Therefore, even when another test object container holder 100 is kept in tight contact with a desired test object container holder 100 in the front side thereof in the forward direction on the convey path, the desired test object container holder 100 can be paused at a predetermined position without influencing another test object container holder 100 in the front side. Thus, for example, pause control of a desired test object container holder 100 can be easily and securely performed.

Further, to detect a test object container holder 100, it is only necessary to detect an indication ring 102 forming a ring shape. As a result, much more accurate detection is achieved in comparison with detection of a test object container holder 100 itself, and detection of a test object container holder 100 (e.g., arrival of a test object container holder at a predetermined position and counting of the number of holders) can always be stably performed when the test object holder 100 being conveyed is oriented in any directions.

[2] The test object container holder 100 of the embodiment is a test object container holder 100 described above in the item [1], wherein the holder body 101 is made of resin material and the indication ring 102 is made of metal.

Therefore, in the test object container holder 100, since the indication member thus has a ring shape, it is natural that stable detection of a test object container holder 100 can be performed regardless of the orientation of the test object container holder 100. Besides, since the indication ring 102 is made of metal, a metal sensor of a low price can be adopted as a sensor. Note that the kind of metal forming the indication ring 102 may be previously selected as a predetermined one in accordance with characteristics of a sensor used. The metal should preferably have an electric conductivity and an appropriate gloss. Since the holder body 101 is made of resin material, it has a slight elasticity and is suitable for holding a glass test object container. Further, the function of this kind of test object container is not affected at all even when the indication ring 102 made of metal material is engaged in the outer circumference thereof.

[3] The test object container holder 100 explained in the embodiment is a test object container holder 100 according to the above item [1] or [2], and the container storage portion 114 comprises a container storage hole 111 provided so as to store a lower region including at least the bottom of the test object container 1, and a connection hole 112 provided so as to connect the bottom inner surface of the container storage hole 111 with the outer surface of the holder body 101.

Therefore, in the above test object container holder 100, air in the storage hole 111 freely enters into and comes out through the connection hole 112 when the test object container 1 such as a test tube is inserted into the container storage hole 111 or pulled out of the container storage hole 111, so that air inside the container storage hole 111 is not compressed or the inside of this hole does not form a vacuum. Thus, insertion and pulling operations for the test object container 1 can be smoothly performed.

[4] The test object container holder 100 explained in the embodiment is a test object container holder 100 according to the above item [3], wherein the connection hole comprises a main connection hole 112 provided along the axis of the cylindrical base 110 and a sub connection hole 113 provided in the direction perpendicular to the main connection hole 112.

Therefore, in the above test object container holder 100, even when the outlet open end of the main connection hole 112 is brought into tight contact with the surface of the convey path and thereby closed, air communicates through the sub connection hole 113, and therefore, insertion and pulling operations for the test object container 1 are not disturbed by compression of air or a vacuum.

[5] The test object container holder 200 explained in the embodiment comprises a holder body 201 and an adapter member 204 for a container of a different diameter. The holder body. 201 includes a container storage portion 214 at an axial portion of a cylindrical base 210, said portion 214 being capable of holding the test container 1, a first ring groove 221 near the top of the outer circumferential surface of the cylindrical base 210, said first ring groove 221 being to be engaged with guide edges 12a and 12b of the convey path, and a second ring groove 222 near the bottom of the outer circumferential surface of the 10 cylindrical base 210, which allows insertion of the operation rod 30L in the convey pause mechanisms 31, 32, 33 . . . .

The adapter member 204 for a container of a different diameter is installed on the open end of the container storage portion 214 and includes a brim-like elastic member which has a projecting portion 241 in its inner peripheral portion of thereof and projects in the direction toward the center thereof.

Therefore, in the test object container holder 200, even when a test tube having a diameter different from other test tubes is used as a test object container 1, such a test object container 1 of different diameter can be contained and held due to the function of the adapter member 204 for a container of different diameter. Specifically, when the test object container 1 is inserted into the container storage portion 214 of the test object container holder 200, the projecting portion 241 of the adapter member 204 is elastically deformed thereby changing the size of the opening portion. Therefore, the test object container 1 can be stably contained and held in the container storage portion 214 of the test object container holder 200.

[6] The test object container holder 200 explained in the embodiment is a test object container holder 200 according to the above item [5], wherein the adapter member 204 for a container of different diameter has a slit-like opening 242 having a cross-like shape.

Therefore, in this test object container holder 200, the shape of the adapter member 204 is very simplified so that the test object container 1 can be held stably and besides, can be easily processed and manufactured at low costs.

[7] The test object container holder 200 is a test object container holder 200 according to the above item [5], wherein the adapter member 204 is detachably mounted on the open end of the container storage portion 214 of the holder body 201.

Therefore, in the above test object container holder 200, the adapter member 204 for a container of different diameter is detachable from the holder body 201, so that the adapter can be replaced with a new one when the member 204 loses an elasticity or is soiled due to long use or when it is necessary to use an adapter having a projecting portion 241 of a different shape or of a different length.

[8] The test object container holder 200 explained in the embodiment is a test object container holder 200 according to the above item [5], wherein an indication ring 202 for indicating presence of the holder body 201 is engaged in the outer circumference of the holder body 200.

Therefore, in the above test object container holder 200, when a test tube or the like having a diameter size different from other containers is used as a test object container 1, the test object container holder 200 of the same type can stably contain and hold the test object container 1 of a different diameter, without problems, like the operation in the item [5]. Simultaneously, since a test object container holder 200 can be detected by merely detecting the indication ring 202 of a shape like a ring, like the operation in the item [1], detection can be performed more accurately in comparison with the case of detecting the test object container holder 200 itself, and besides, the test object container holder 200 can always be stably detected regardless of the direction in which the test object container 1 is oriented.

[9] The test object container holder 200 explained in the embodiment is a test object container holder 200 according to the above item [8], and further comprises a fixed cap 203 which comprises a cylindrical portion 203a which can be screwed on the top of the holder body 201 and a fringe portion 203b projecting into the top end of the cylindrical portion 203a. The cap 203 presses the indication ring 202 engaged in the outer circumference of the holder body 201 with the base end portion of the cylindrical portion 203a, and simultaneously, presses the peripheral portion of the 10 adapter member 204 for a container of a different diameter attached to the open end of the container storage portion 214 with the fringe portion 203b projecting into the top end of the cylindrical portion 203a.

Therefore, in the test object container holder 200, if only one single fixed cap 203 is screwed on the top of the holder body 201, the indication ring 202 engaged in the outer circumference of the holder body 201 and the adapter member 204 for containers of a different diameter attached to the opening end of the container storage portion 214 can be simultaneously fixed. As a result of this, even a test object container holder 200 having various functions can reduce complication of the structure to the lower limit and can maintain its simple shape.

[10] The test object container holder conveyer apparatus explained in the embodiment comprises a test object container holder (100, 200), a holder conveyer means 10, a holder detection sensors 21, 22, 23 . . . ., convey pause mechanisms 31, 32, 33 . . . , an orientation control mechanism 50, a read device 40, and a command means (60, 33, 34).

The test object container holder (100, 200) includes a holder body (101, 201) and an indication ring (102, 202). The holder body (101, 201) has a container storage portion (114, 214) at an axial portion of a cylindrical base (110, 210), said container storage portion being capable of holding the test object container 1, a first ring groove 121 near the top of the outer circumferential surface of the cylindrical base (110, 210), said first ring groove 121 being to be engaged with guide edges 12a and 12b of the convey path, and a second ring groove 122 near the bottom of the outer circumferential surface of the cylindrical body (110, 210), which allows insertion of the operation rod 30L in the convey pause mechanisms 31, 32, 33 . . . . The indication ring (102, 202) is engaged in the outer circumference of the holder body (101, 201) and is used to indicate presence of the holder body (101, 201).

The holder conveyer means 10 comprises a conveyer mechanism 11 provides so as to be capable of conveying the test object container holder (100, 200), and guide mechanism 12 provided such that guide edge portions 12a and 12b of the upper end of the side wall portions 12A and 12B provided so as to stand on both sides of the conveyer mechanism 11 are engaged with the first ring groove (121, 221) of the test object container holder (100, 200).

The holder detection sensors 21, 22, 23 . . . , which detect the indication ring 102 of the test object container holder 100 conveyed to a specified position by the holder conveyer means 10 and outputs information 10 indicating the test object container holder (100, 200) has arrived at the specified position; the convey pause mechanism 31, 32, 33 . . . are operated on the basis of the output from these sensors 21, 22, 23 . . . ., thereby to insert an operation rod 30L into an area positioning in the forward side of the holder (100, 200) in the forward direction in the second groove (121, 221) of the test object container holder (100, 200).

The orientation control mechanism 50 controls the test object container holder (100, 200) paused by the convey pause mechanisms 31, 32, 33 . . . , such that an information record area 2 of the test object container 1 stored and held by the holder (100, 200) is oriented in a predetermined direction, by rotating the holder around the holder axis as the center of rotation.

The read device 40 is provided so as to read record information 3 of the information record area 2 whose orientation is controlled by the orientation control mechanism 50.

The command means (60, 33, 34) supplies the test object container holder (100, 200) with a necessary command on the basis of the information read by the read device 40.

Therefore, in the test object container holder conveyer apparatus, when the test object container holder (100, 200) containing and storing the test object container 1 is conveyed to a specified position by the conveyer mechanism 11, the indication ring (102, 202) of the test object container holder (100, 200) is accurately detected by the sensors 21, 22, and 23, which output a signal indicating arrival of the test object container holder (100, 200). Then, the convey pause mechanism is operated so as to insert the operation rod 30L into an area of the second ring groove (122, 222) positioned in the forward side of the holder (100, 200) in the forward direction of the holder (100, 200), so that the test object container holder (100, 200) is paused at the specified position. The test object container holder (100, 200) thus paused is driven to rotate around the holder axis as the center of rotation by the orientation control mechanism 50, and is controlled such that the information record area (e.g., the stuck area of the bar-code label) is oriented in a predetermined direction (i.e., the sensor arrangement direction).

As control manners for orienting the information record area 2 in a predetermined direction, there are two cases, i.e., one is the case in which the test object container holder (100, 200) is merely continuously rotated thereby to make the information record area 2 relatively scanned by the read device 40 oriented in a predetermined direction, while another is the case in which the area 2 is once stopped during rotation at a position where the area 2 faces the sensor oriented in a predetermined direction. The record information (e.g., a bar-code) recorded on the information record area whose orientation is controlled is read by the read device 40 (e.g., a bar-code reader). Based on the information thus read, the test object container holder (100, 200) is supplied with a necessary command (e.g., a command for moving a corresponding test object container holder to a predetermined other convey path thereby to assort holders).

[11] The test object container holder conveyer apparatus explained in the embodiment is a test object container holder conveyer apparatus according to the above item [10] and uses a belt-type conveyer mechanism 11 as the conveyer mechanism, wherein conveying operation is paused at a specified position with the test object container holder (100, 200) slipping on the specified position, by operating the convey pause mechanisms 31, 32, 33 . . . with the belt 13 of the belt-type conveyer mechanism 11 being moved.

Therefore, in the above test object container holder convey apparatus, only a predetermined test object container holder (100, 200) can be paused at a specified position with the conveyer mechanism 11 being operated, so that other test object container holders than the predetermined test object container holder (100, 200) can be continuously conveyed. In addition, since the conveyer mechanism 11 does not frequently repeat start and stop operations, it is possible to reduce generation of noise and damages of respective components accompanied by start and stop operations of the conveyer mechanism 11.

[12] The test object container holder conveyer apparatus explained in the embodiment is a test object container holder conveyer apparatus according to the above item [11], and orientation control mechanism 50 comprises a means for pressing downwardly the top eccentric position of the test object container holder (100, 200) paused at a specified position, slipping on the belt 13, thereby to incline the test object container holder 100 to apply a rotation torque based on the belt movement.

Therefore, in the above test object container holder conveyer apparatus, when the top eccentric position of the test object container holder (100, 200) is moved downwardly, thereby inclining the test object container holder (100, 200), a deviated portion of the bottom of the test object container holder (100, 200) is more strongly pressed against the belt 13 of the conveyer mechanism in comparison with the other portions. Thus, a rotation torque based on the moving force of the belt 13 is generated at the test object container holder (100, 200) paused at a specified position, so that the test object container holder (100, 200) is driven to rotate. Hence, it is not necessary to provide any special driving source, the structure of the apparatus is simplified accordingly.

What is claimed is:

1. A test object container holder comprising:

a holder body including a cylindrical base, a container storage portion capable of storing a test object container, provided in an axial portion of the cylindrical base, a first ring groove near the top of an outer circumferential surface of the cylindrical base, to be engaged with guide edges of a convey path, and a second ring groove near the bottom of the outer circumferential surface of the cylindrical base, which allows insertion of an operation rod by a convey pause mechanism provided at the convey path; and an indication ring engaged in the outer circumference of the holder body for indicating presence of the holder body.

2. A test object container holder according to claim 1, wherein the holder body is made of resin material and the indication ring is made of metal.

3. A test object container holder according to claim 1, wherein the container storage portion comprises a container storage hole provided such that the container storage hole is capable of storing a lower area of the test object container including at least a bottom thereof, and of a connection hole provided so as to connect a bottom inner surface of the container storage hole with an outer surface of the holder body.

4. A test object container holder according to claim 2, wherein the container storage portion comprises a container storage hole provided such that the container storage hole is capable of storing a lower area of the test object container including at least a bottom thereof, and of a connection hole provided so as to connect a bottom inner surface of the container storage hole with an outer surface of the holder body.

5. A test object container holder comprising:

a holder body including a cylindrical base, a container storage portion capable of storing a test object container, provided in an axial portion of the cylindrical base, a first ring groove near the top of an outer circumferential surface of the cylindrical base, to be engaged with guide edges of a convey path, and a second ring groove near the bottom of the outer circumferential surface of the cylindrical base, which allows insertion of an operation rod by a convey pause mechanism provided in the convey path; and an adapter member for a container of different diameter attached to an open end of the container storage portion in the holder body, and formed of a brim-like elastic member having a projecting portion provided in an inner peripheral portion of the elastic member and projecting in a direction toward the center thereof.

6. A test object container holder according to claim 5, wherein an indication ring for indicating presence of the holder body is engaged in an outer circumference of the holder body.

7. A test object container holder conveyer apparatus comprising:

a test object container holder including a holder body having a cylindrical base, a container storage portion capable of storing a test object container, provided in an axial portion of the cylindrical base, a first ring groove near the top of an outer circumferential surface of the cylindrical base, to be engaged with guide edges of a convey path, and a second ring groove near the bottom of the outer circumferential surface of the cylindrical base, which allows insertion of an operation rod by a convey pause mechanism provided in the convey path, and an indication ring engaged in the outer circumference of the holder body for indicating presence of the holder body;

a holder conveyer means including a conveyer mechanism provided so as to be capable of conveying the test object container holder, and a guide mechanism provided on both sides of the conveyer mechanism such that guide edge portions of upper ends of side wall portions are engaged with the first ring groove of the test object container holder;

holder detection sensors which detect the indication ring of the test object container holder conveyed to a specified position by the holder conveyer means and output information indicating arrival of the test object container holder at the specified portion;

said convey pause mechanism is operated on the basis of an output from these sensors, so as to insert said operation rod into the second groove at the forward side of the holder;

an orientation control mechanism for controlling the test object container holder paused by the convey pause mechanism such that an information record area of the test object container contained and held by the holder is oriented in a predetermined direction, by rotating the holder around a holder axis as the center of rotation;

a read device provided so as to read record information of the information record area whose orientation is controlled by the orientation control mechanism; and a command means for supplying the test object container holder with a necessary command on the basis of the information read by the read device.

8. A test object container holder conveyer apparatus according to claim 7, wherein a belt-type conveyer mechanism is used as the conveyer mechanism, and the convey pause mechanism is operated with a belt of the belt-type conveyer mechanism being moved, thereby to pause convey operation at a specified position with the test object container holder slipping at the specified position on the belt.

9. A test object container holder conveyer apparatus according to claim 7, wherein a belt-type conveyer mechanism is used as the conveyer mechanism, and the convey pause mechanism is operated with a belt of the belt-type conveyer mechanism being moved, thereby to pause convey operation at a specified position with the test object container holder slipping at the specified position on the belt, and the orientation control mechanism includes means for pressing downwardly a top eccentric position of the test object container holder paused at the specified position, slipping on the belt, thereby to incline the test object container holder to apply a rotation torque based on the belt movement.

* * * * *